United States Patent [19]

Borschneck

[11] 4,350,153

[45] Sep. 21, 1982

[54] SPLINT FOR USE WITH A HUMAN LEG

[76] Inventor: Anthony G. Borschneck, 15649 Prospect Dr., Redding, Calif. 96001

[21] Appl. No.: 289,776

[22] Filed: Aug. 3, 1981

[51] Int. Cl.³ .............................................. A61F 5/04
[52] U.S. Cl. ................................................. 128/84 C
[58] Field of Search ................ 128/75, 84 R, 84 C, 128/87 R, 85; 242/74.1, 96, 99, 107.4 A

[56] References Cited

U.S. PATENT DOCUMENTS

| | | | |
|---|---|---|---|
| 3,662,750 | 5/1972 | Jorgensen | 128/75 |
| 3,756,227 | 9/1973 | Sager | 128/85 |
| 3,906,942 | 9/1975 | Lumb, Jr. et al. | 128/85 |
| 4,079,734 | 3/1978 | Bergin et al. | 128/84 C |

Primary Examiner—John D. Yasko
Attorney, Agent, or Firm—Lothrop & West

[57] ABSTRACT

A splint for use with a human leg has a frame including a pair of rod portions adapted to extend in one direction along a leg. At one end the frame has a pad for engagement with the ischial tuberosity. At the other end the frame carries a base block in engagement with which is a sliding block, the blocks being relatively movable in the indicated direction by a screw with an operating knob. A cable is attached to the leg in the ankle region and engages one end of a spring structure at the other end engaging the sliding block. An indicator shows the relative position of the cable and of the sliding block.

9 Claims, 5 Drawing Figures

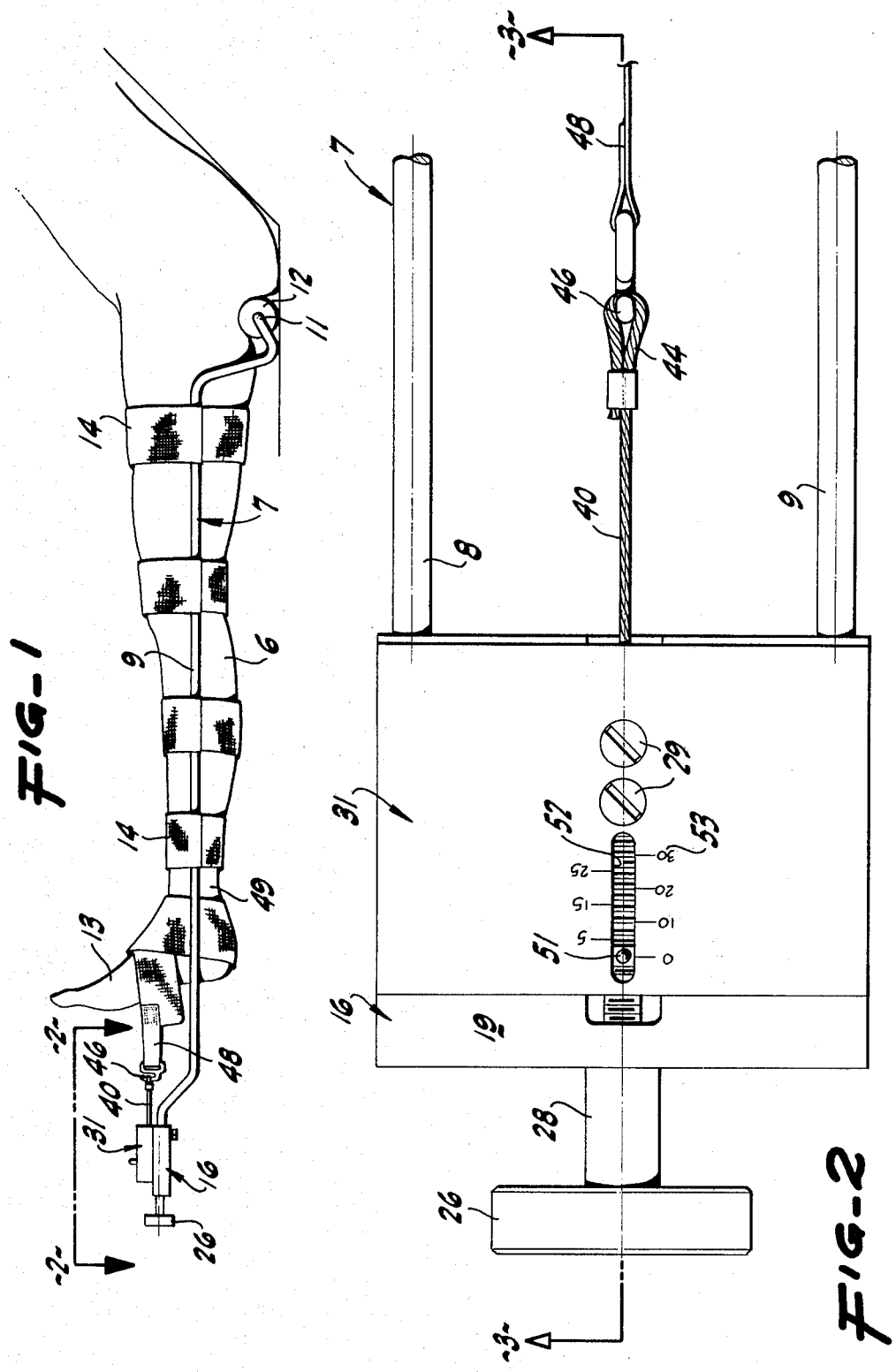

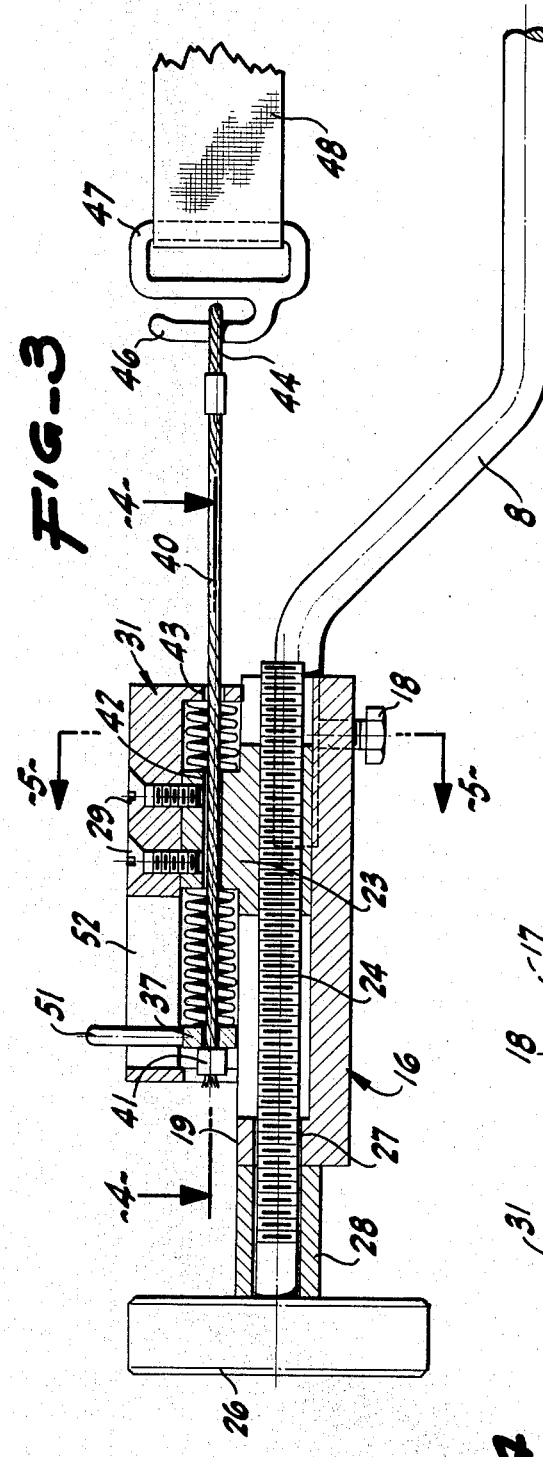

4,350,153

SPLINT FOR USE WITH A HUMAN LEG

BACKGROUND OF THE INVENTION

In caring for injured people, particularly those with a broken leg, it is highly helpful to have a splint that can be made readily available, that is light, easily applied and set up, and that is effective to hold the broken bone portions in proper position as long as needed, that is relatively comfortable for the patient, and that can be removed without difficulty.

BRIEF SUMMARY OF THE INVENTION

While numerous splints for human use have been available for many years, there are still adequate regions for improvement in that the size and cumbersomeness of the splints can be reduced, the weight and packing factors can be improved, the ability to use the splint quickly, easily and without damage to the patient can also be improved, and further the particular means for placing traction on the leg and indicating the amount of traction can readily now be provided.

It is therefore an object of the invention to provide a generally improved leg splint for human use.

Another object of the invention is to provide a human leg splint which is light in weight, easy to handle, and can readily be disassembled for packing and assembled for use.

An additional object of the invention is to provide a splint affording a readily indicated amount of traction on the limb being treated.

A further object of the invention is to provide a splint in which contact with the injured limb is favorably accomplished.

Other objects together with the foregoing are attained in the embodiment of the invention described in the accompanying description and illustrated in the accompanying drawings.

BRIEF DESCRIPTION OF THE SEVERAL VIEWS OF THE DRAWINGS

FIG. 1 is a side elevation of the splint as applied for effective use in connection with a human leg.

FIG. 2 is a plan view to an enlarged scale of the structure of FIG. 1 and as indicated by the line 2—2 of FIG. 1.

FIG. 3 is a cross-section, the plane of which is indicated by the line 3—3 of FIG. 2.

FIG. 4 is a plan of some of the structure shown in FIG. 3, the plane of the view being indicated by the line 4—4 of FIG. 3.

FIG. 5 is a cross-section, the plane of which is indicated by the line 5—5 of FIG. 3.

DETAILED DESCRIPTION

The splint of the present arrangement is especially adapted for use on a leg 6 of a human and preferably comprises a main frame 7 including side rod portions 8 and 9 at one end joined to provide a cross rod 11 carrying a pad 12 or covering adapted to seat generally in the crotch region, particularly against the ischial tuberosity. The rod portions 8 and 9 extend generally in a predetermined direction and occupy substantially the same transverse plane along the entire length of the leg 6 and actually to a point considerably below the foot portion 13 thereof.

The rod portions 8 and 9 and in effect the entire splint are held in appropriate position by bands 14 disposed around the rods 8 and 9 and the intervening leg 6 and are arranged at suitable intervals to afford a splint mounting substantially stationary on the leg.

At their ends opposite the pad 12 the rod portions extend into a base block 16 of a generally rectangular configuration and inclusive of recesses 17 for receiving the ends of the rods 8 and 9. These are preferably anchored removably in place by set screws 18. By this means the block can be mounted on or removed from the rods quite easily, although when in position can be firmly held. The block 16 has at least an upper planar face 19 and a longitudinally extending central channel 21 enlarged at the bottom to afford a pair of undercut portions 22.

Slidably disposed in the channel 21 and the undercut portions 22 is a sliding block 23 having keys engaged in the undercut portions 22. To move the sliding block 23 with respect to the base block 16 there is afforded a screw shaft 24 having an actuating knob 26 at one end thereof and extending into the central channel 21 through a bore 27 and being appropriately spaced from the block 23 by an interposed sleeve 28.

The screw shaft 24 is in threaded engagement with the sliding block 23 so that rotation of the screw shaft can produce corresponding rectilinear motion of the slider relative to the base block. Preferably, the pitch of the threads interengaging the screw shaft and the slider is at a non-overhauling angle, so that while the rotation of the screw shaft can move the slider, the slider cannot be moved endwise to rotate the screw shaft.

The slider is fastened by screws 29 to a movable spring block 31 having a lower planar face 32 in substantial sliding abutment with the upper face 19 of the base block 16.

Disposed in the spring block 31 is a pair of coil springs 33 and 34 at one end resting against the slider block, being positioned in a channel 35 and centralized by pins 36. At the other end the springs 33 and 34 rest against a yoke 37 carrying pins 38 for positioning the springs. The yoke 37 has a central aperture 39 through which passes a cable 40 having an anchor 41 at one end thereof in abutment with the yoke 37. The cable extends through an opening 42 in the sliding block 23 and through a similar opening 43 in the block 31. The cable goes to an eye 44 formed at the end of the cable and surrounds a prong 46 on a loop 47 of a strap 48 properly surrounding and in engagement with the ankle portion 49 of the leg 6.

With this arrangement, when the splint is applied as shown in FIG. 1, the user, by rotating the knob 26 in the proper direction, can slide the spring block 31 in a direction to impose tension on the cable 40 through the pair of springs 33 and 34. Through the strap 48 this imposes a force on the ankle portion of the leg and so puts tension on the entire leg structure so that the fractured bones can be brought into alignment.

The amount of rotation of the knob 26 that is appropriate under the circumstances is shown by an indicator rod 51 acting in a slot 52 in the spring block 31. The rod moves opposite a scale 53 graduated in any desired units, such as pounds or grams. Thus, by observing the rod 51 or pointer with respect to the graduations 53, the user can turn the knob 26 in the proper direction to impress or impose the desired or recommended amount of tension through the cable 40 and so onto the leg 6. When the purpose of the splint has been served, it is easily removed by relaxing the tension by appropriate rotation of the knob 26, by removing the various bandages 14 or straps, and by removing the ankle strap 48. If the device is not to be immediately reused and must be stored, it is simple to relax the set screws 18 and detach the rod portions 8 and 9 from the base block 16 and so compact the entire device for future assembly and use.

Although the device heretofore described and illustrated in FIGS. 1–5 comprises a splint utilizing side rods 8 and 9 which terminate in ends located in sockets 17 in the base block 16, it should also be recognized that full ring or half ring splints of the Thomas type can also readily be utilized in conjunction with the present traction device.

In other words, since the side rods of both the full ring and the half ring Thomas splints are joined at the foot end, it is merely necessary to mount a pair of brackets (not shown), of any suitable configuration, on the bottom or sides of the base block 16. The splint rods are selectively clamped to or unclamped from the base block by any one of several appropriate fastening means, such as one or more machine screws (not shown) interconnecting the brackets and the base block.

I claim:

1. A splint for use with a human leg comprising a frame adapted to extend in a predetermined direction from the region of the crotch to a location beyond the foot, means on one end of said frame for abutment with the ischial tuberosity, a base block on the other end of said frame, a sliding block, means interrelating said base block and said sliding block for relative movement in said predetermined direction, means adapted to engage the leg in the ankle region, a spring structure interposed between said means engaging the leg in said ankle region and said sliding block, and means interengaging said sliding block and said base block for moving said sliding block relative to said base block to vary the tension of said spring structure.

2. A splint as in claim 1 in which said frame includes a pair of rod portions adapted to lie in a transverse plane, and said base block has a first planar face and engages both of said rod portions to dispose said first planar face parallel to said transverse plane.

3. A splint as in claim 2 in which said sliding block has a second planar face, and means for holding said second planar face in substantial sliding abutment with said first planar face.

4. A splint as in claim 1 in which said means for moving said sliding block relative to said base block includes a screw adapted to rotate relative to said base block and having a threaded engagement with said sliding block.

5. A splint as in claim 4 in which said threaded engagement includes threads of a non-overhauling pitch.

6. A splint as in claim 1 including means for indicating the relative position of said sliding block and said leg engaging means.

7. A splint as in claim 6 in which said indicating means includes a calibrated slot in said sliding block and an indicator pin on said leg engaging means and movable in said slot.

8. A splint as in claim 1 in which said sliding block has a channel therethrough, and said leg engaging means includes a cable extending through said channel and into engagement with said spring structure.

9. A splint as in claim 8 in which said spring structure includes a pair of spring coils abutting said sliding block and disposed on opposite sides of said cable, and a yoke abutting said pair of spring coils and engaging said cable.

* * * * *